United States Patent
Murooka (10) Patent No.: US 10,551,607 B2
(45) Date of Patent: Feb. 4, 2020

(54) IMAGING APPARATUS AND METHOD AND IMAGING CONTROL PROGRAM

(71) Applicant: FUJIFILM Corporation, Tokyo (JP)

(72) Inventor: Takashi Murooka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 246 days.

(21) Appl. No.: 15/790,631

(22) Filed: Oct. 23, 2017

(65) Prior Publication Data

US 2018/0129028 A1    May 10, 2018

(30) Foreign Application Priority Data

Nov. 9, 2016 (JP) .................................. 2016-218837

(51) Int. Cl.
*G02B 21/02* (2006.01)
*C12M 1/34* (2006.01)
*G01N 33/50* (2006.01)

(52) U.S. Cl.
CPC ........... *G02B 21/025* (2013.01); *C12M 41/46* (2013.01); *G01N 33/5073* (2013.01)

(58) Field of Classification Search
None
See application file for complete search history.

(56) References Cited

U.S. PATENT DOCUMENTS

| | | | | |
|---|---|---|---|---|
| 8,654,427 B1 * | 2/2014 | DeAngelo | ............ | G02B 7/004 359/221.2 |
| 9,587,219 B2 * | 3/2017 | Kuroda | ............ | C12M 23/08 |
| 2017/0010455 A1 | 1/2017 | Tsujimoto | | |

FOREIGN PATENT DOCUMENTS

| | | | | |
|---|---|---|---|---|
| JP | 7-131688 A | 5/1995 | | |
| JP | 2006-187206 A | 7/2006 | | |
| JP | 2010014494 | * 1/2010 | ............ | G01N 21/17 |
| JP | 2011-127972 A | 6/2011 | | |
| JP | 2011-141444 A | 7/2011 | | |
| JP | 2016-91004 A | 5/2016 | | |
| JP | 2015-194544 A | 11/2016 | | |

OTHER PUBLICATIONS

JP 62-069979 Hirokazu et al Sep. 20, 1985 English translation (Year: 1985).*

(Continued)

*Primary Examiner* — Nancy Bitar (74) *Attorney, Agent, or Firm* — Birch, Stewart, Kolasch & Birch, LLP (57) ABSTRACT

An imaging apparatus includes: an imaging apparatus main body for imaging an observation target contained in a container; and a liquid droplet adhesion determination unit that acquires pattern information of liquid droplets adhering to a bottom surface on an outer side of the container based on an image of the observation target imaged by the imaging apparatus main body and determines whether or not the liquid droplets adhere to the bottom surface based on the pattern information. In a case where the liquid droplet adhesion determination unit determines that the liquid droplets adhere to the bottom surface on the outer side of the container, the imaging apparatus main body images the observation target again after performing liquid droplet removal processing.

20 Claims, 5 Drawing Sheets

(56) References Cited

OTHER PUBLICATIONS

JP 2004-245727 Jun et al Feb. 14, 2003 ENglish translation (Year: 2003).*
JP 05-181068 Kunitoshi et al English translation Aug. 20, 1991 (Year: 1991).*
Japanese Office Action for corresponding Japanese Application No. 2016-218837, dated Nov. 5, 2019, with English translation.

* cited by examiner

IMAGING APPARATUS AND METHOD AND IMAGING CONTROL PROGRAM

CROSS-REFERENCE TO RELATED APPLICATIONS

The present application claims priority under 35 U.S.C. § 119 to Japanese Patent Application No. 2016-218837, filed on Nov. 9, 2016. Each of the above application(s) is hereby expressly incorporated by reference, in its entirety, into the present application.

BACKGROUND OF THE INVENTION

1. Field of the Invention

The present invention relates to an imaging apparatus and method for imaging an observation target contained in a container and a non-transitory computer readable recording medium storing an imaging control program.

2. Description of the Related Art

Pluripotent stem cells, such as embryonic stem (ES) cells and induced pluripotent stem (iPS) cells, have the ability to differentiate into cells of various tissues. Accordingly, since the pluripotent stem cells can be applied in regenerative medicine, development of medicine, elucidation of disease, and the like, the pluripotent stem cells have been drawing attention.

In the related art, a method of imaging pluripotent stem cells such as ES cells and iPS cells, differentiation-induced cells, or the like using a microscope or the like and determining the differentiation state of cells by ascertaining the features of the image has been proposed.

Pluripotent stem cells, such as ES cells and iPS cells, are contained in a culture container, such as a well plate, and are cultured under the conditions in which the environmental temperature and the environmental humidity are managed in an incubator. Then, in the case of capturing an image of the cultured pluripotent stem cells, the culture container is supplied from the incubator to the microscope.

SUMMARY OF THE INVENTION

In the case of moving the culture container from the incubator to the microscope as described above, dew condensation occurs due to differences in temperature and humidity between the incubator and the outside air. As a result, liquid droplets adhere to the bottom surface on the outer side of the culture container. Since the liquid droplet has a size of about 30 µm to 100 µm, the liquid droplet cannot be checked with the naked eye. For this reason, cells in the culture container are imaged as they are without being noticed by the operator of the microscope.

However, in the case of imaging cells with liquid droplets adhering to the bottom surface, there is a problem that the focal position of light passing through the cells is shifted due to the liquid droplets and accordingly a blurred image is generated. As one of autofocus control methods of the microscope, there is a method of performing autofocus control by emitting striped pattern light to a culture container and detecting an image of the pattern light with a line sensor or the like. However, even if such autofocus control is performed, in a case where liquid droplets adhere to the culture container as described above, the imaging position of the pattern light on the line sensor is shifted. As a result, since the autofocus control cannot be appropriately performed, there is also a problem that a blurred image is generated.

JP2011-141444A discloses a method of detecting liquid droplets adhering to a lid of a culture container. Specifically, JP2011-141444A discloses a method of detecting liquid droplets adhering to the lid of the culture container by superimposing a mask image, which has a shape of an image of the phase difference aperture diaphragm of a phase contrast microscope, and an image, which is imaged by inserting a Bertrand lens into the optical path of the phase contrast microscope, and calculating the sum of the brightness at the time of superimposition. However, it is presumed that the liquid droplet, which is a problem in JP2011-141444A, adheres to the lid of the culture container and is not a liquid droplet having a size that cannot be checked with the naked eye as described above. That is, since the liquid droplet that is a problem in JP2011-141444A has a size that can be checked with the naked eye, the presence or absence of liquid droplets is detected by detecting stray light generated by the liquid droplets in JP2011-141444A.

However, in a case where the liquid droplet has a size that cannot be checked with the naked eye, a brightness change due to stray light is not obtained in the method disclosed in JP2011-141444A. Accordingly, it is not possible to detect liquid droplets.

JP2011-127972A discloses a method of detecting culture liquid droplets. However, these culture liquid droplets are completely different from the above-described liquid droplets that cannot be checked with the naked eye.

In view of the above problems, it is an object of the invention to provide an imaging apparatus and method and a non-transitory computer readable recording medium storing an imaging control program capable of suppressing blurring due to liquid droplets that adhere to the bottom surface on the outer side of a container and have sizes that cannot be checked with the naked eye.

An imaging apparatus of the invention comprises: an imaging unit that images an observation target contained in a container; and a liquid droplet adhesion determination unit that acquires pattern information of liquid droplets adhering to a bottom surface on an outer side of the container based on an image of the observation target imaged by the imaging unit and determines whether or not the liquid droplets adhere to the bottom surface based on the pattern information. In a case where the liquid droplet adhesion determination unit determines that the liquid droplets adhere to the bottom surface on the outer side of the container, the imaging unit images the observation target again after performing a liquid droplet removal processing.

In the imaging apparatus of the invention described above, the imaging unit may image the observation target by performing autofocus control.

In the imaging apparatus of the invention described above, the liquid droplet adhesion determination unit may acquire spatial frequency components included in the image as the pattern information, and determine whether or not the liquid droplets adhere to the bottom surface on the outer side of the container based on the spatial frequency components.

In the imaging apparatus of the invention described above, the liquid droplet adhesion determination unit may acquire a bright and dark pattern included in the image as the pattern information, and determine whether or not the liquid droplets adhere to the bottom surface on the outer side of the container based on the bright and dark pattern.

In the imaging apparatus of the invention described above, the liquid droplet adhesion determination unit may acquire spatial frequency components and a bright and dark pattern, which are included in the image, as the pattern information, and determine whether or not the liquid droplets adhere to the bottom surface on the outer side of the container by performing first determination based on the spatial frequency components and then performing second determination based on the bright and dark pattern.

In the imaging apparatus of the invention described above, the liquid droplet adhesion determination unit may acquire the pattern information by recognizing a pattern of the liquid droplets included in the image, and determine whether or not the liquid droplets adhere to the bottom surface on the outer side of the container based on the pattern information.

In the imaging apparatus of the invention described above, the liquid droplet adhesion determination unit may have a machine-learned discriminator for discriminating the liquid droplets, and recognize the pattern of the liquid droplets using the discriminator.

In the imaging apparatus of the invention described above, the liquid droplet removal processing is processing for leaving the container in an incubator, in which the container is contained, for a preset time.

The imaging apparatus of the invention described above may further comprise a liquid droplet removal processing unit that performs the liquid droplet removal processing.

In the imaging apparatus of the invention described above, the liquid droplet removal processing unit may have a wiping unit for wiping out the liquid droplets on the bottom surface on the outer side of the container.

In the imaging apparatus of the invention described above, the liquid droplet removal processing unit may have a heating unit for increasing a temperature of the bottom surface of the container.

In the imaging apparatus of the invention described above, the liquid droplet removal processing unit may have an air supply unit for supplying air toward the bottom surface of the container.

An imaging method of the invention comprises: imaging an observation target contained in a container; acquiring pattern information of liquid droplets adhering to a bottom surface on an outer side of the container based on an image of the imaged observation target and determining whether or not the liquid droplets adhere to the bottom surface based on the pattern information; and imaging the observation target again after performing a liquid droplet removal processing in a case where it is determined that the liquid droplets adhere to the bottom surface on the outer side of the container.

A non-transitory computer readable recording medium storing an imaging control program of the invention causes a computer to function as: an imaging control unit that controls an imaging unit to image an observation target contained in a container; and a liquid droplet adhesion determination unit that acquires pattern information of liquid droplets adhering to a bottom surface on an outer side of the container based on an image of the observation target imaged by the imaging unit and determines whether or not the liquid droplets adhere to the bottom surface based on the pattern information. In a case where the liquid droplet adhesion determination unit determines that the liquid droplets adhere to the bottom surface on the outer side of the container, the imaging control unit controls the imaging unit to image the observation target again after performing a liquid droplet removal processing.

According to the imaging apparatus and method and the non-transitory computer readable recording medium storing the imaging control program of the invention, the observation target contained in the container is imaged, pattern information of liquid droplets adhering to the bottom surface on the outer side of the container is acquired based on the image of the imaged observation target, and it is determined whether or not the liquid droplets adhere to the bottom surface based on the pattern information. Then, in a case where it is determined that liquid droplets adhere to the bottom surface on the outer side of the container, the observation target is imaged again after performing the liquid droplet removal processing. As a result, it is possible to suppress blurring due to liquid droplets that adhere to the bottom surface on the outer side of the container and have sizes that cannot be checked with the naked eye.

DESCRIPTION OF THE PREFERRED EMBODIMENTS

Figure 1:
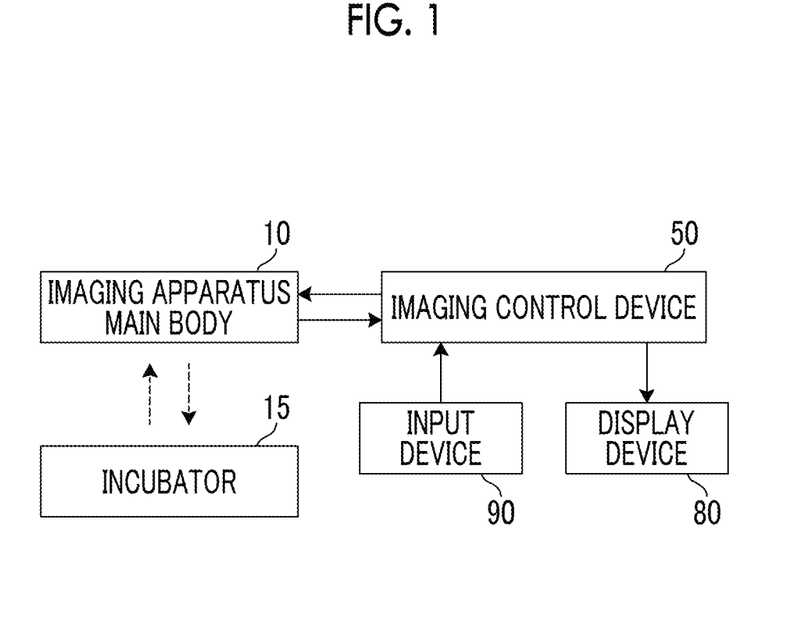
FIG. 1 is a block diagram showing the schematic configuration of a microscope system using an embodiment of an imaging apparatus of the invention.

Hereinafter, a microscope system using an embodiment of an imaging apparatus and method and a non-transitory computer readable recording medium storing an imaging control program of the invention will be described in detail with reference to the diagrams. FIG. 1 is a diagram showing the schematic configuration of the microscope system of the present embodiment.

As shown in FIG. 1, the microscope system of the present embodiment includes an imaging apparatus main body 10, an incubator 15, an imaging control device 50, a display device 80, and an input device 90. The imaging apparatus main body 10 corresponds to an imaging unit of the invention. In the present embodiment, the imaging apparatus of the invention is configured to include the imaging apparatus main body 10 and the imaging control device 50.

The imaging apparatus main body 10 images an image of cells that are observation targets cultured in the incubator 15. The incubator 15 has a culture container (corresponding to a container of the invention) in which cells to be cultured are contained, and manages the environmental temperature and the environmental humidity of the culture container. Between the imaging apparatus main body 10 and the incubator 15, a transport mechanism (not shown) for transporting the culture container is provided. By the transport mechanism, the culture container taken out from the incubator 15 is supplied to the imaging apparatus main body 10 or the culture container is returned from the imaging apparatus main body 10 to the incubator 15. As the transport mechanism, a known mechanism, such as a robot arm and a transport belt, can be used.

Figure 2:
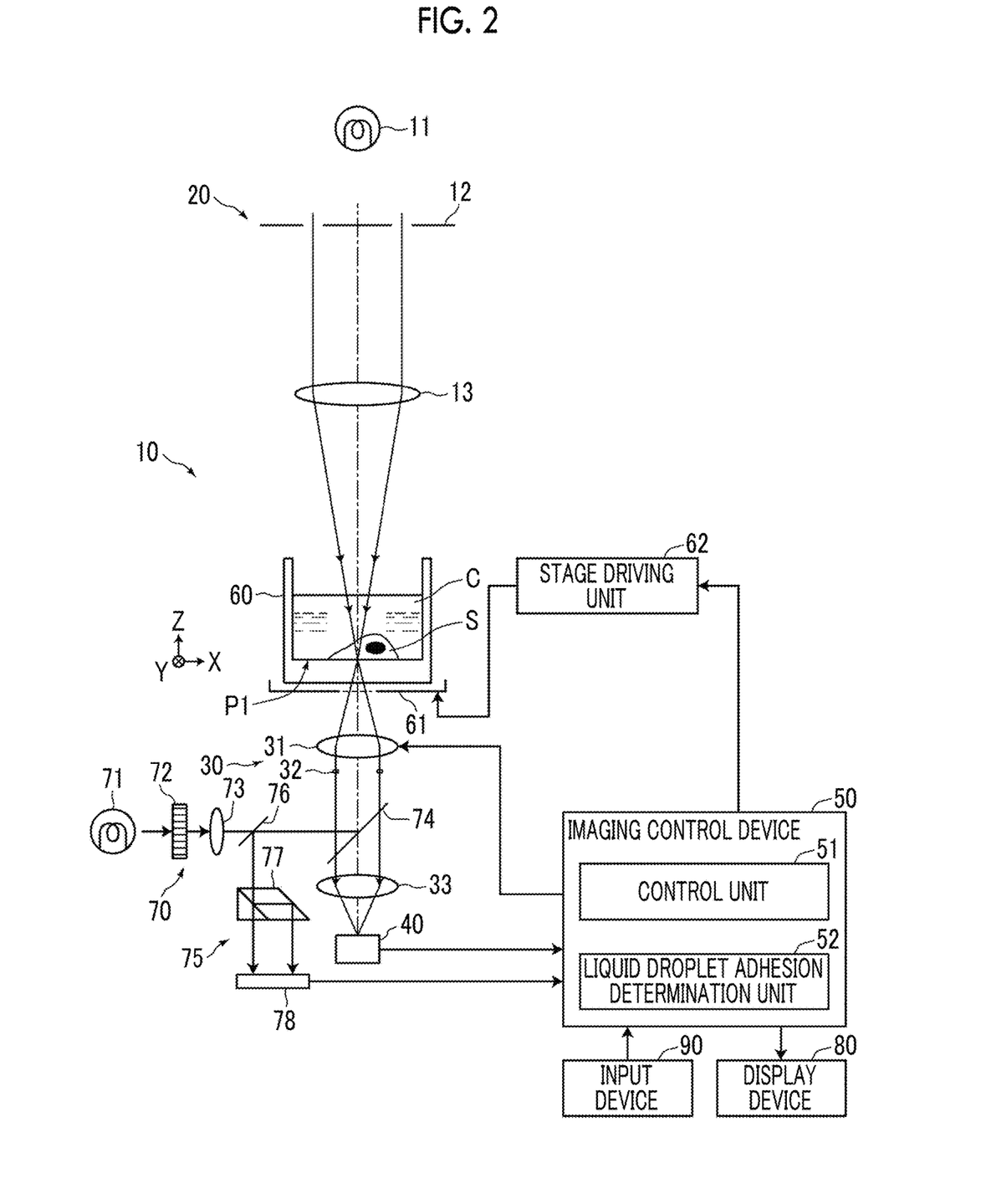
FIG. 2 is a diagram showing the specific configuration of an imaging apparatus main body and an imaging control device.

FIG. 2 is a diagram showing the specific configuration of the imaging apparatus main body 10 and the imaging control device 50. As shown in FIG. 2, the imaging apparatus main body 10 includes an illumination light emission unit 20, an imaging optical system 30, an imaging element 40, a focusing light emission unit 70, a reflected light detection unit 75, a stage 61, and a stage driving unit 62.

In the microscope system of the present embodiment, the stage 61 is provided between the illumination light emission unit 20 and the imaging optical system 30, and a culture container 60 is supported by being placed on the stage 61. In the culture container 60, a culture solution C and an observation target S are contained.

The stage driving unit 62 moves the stage 61 in X, Y, and Z directions. The X and Y directions are directions perpendicular to each other on a plane parallel to an observation target placement surface P1, and the Z direction is a direction perpendicular to the X and Y directions.

The illumination light emission unit 20 emits illumination light for so-called phase difference measurement to the observation target S contained in the culture container 60. In the present embodiment, the illumination light emission unit 20 emits ring-shaped illumination light as the illumination light for phase difference measurement. Specifically, the illumination light emission unit 20 of the present embodiment includes: a white light source 11 that emits white light for phase difference measurement; a slit plate 12 which has a ring-shaped slit, on which the white light emitted from the white light source 11 is incident, and which emits ring-shaped illumination light; and a condenser lens 13 on which the ring-shaped illumination light emitted from the slit plate 12 is incident and which emits the incident ring-shaped illumination light to the observation target S.

The slit plate 12 is obtained by providing a ring-shaped slit, through which white light is transmitted, on a light screen for shielding the white light emitted from the white light source 11. The white light passes through the slit to form ring-shaped illumination light.

In the culture container 60 placed on the stage 61, a cell group or the like is contained as the observation target S. Examples of the culture container 60 include a Petri dish and a well plate in which a plurality of wells are arranged.

The imaging optical system 30 includes an objective lens 31, a phase plate 32, and an imaging lens 33.

The phase plate 32 is obtained by forming a phase ring on a transparent plate that is transparent for the wavelength of the ring-shaped illumination light. The size of the slit of the slit plate 12 described above and the phase ring are in the conjugate relationship.

The phase ring is obtained by forming a phase film, which shifts the phase of incident light by ¼ wavelength, and a dimming filter, which is for dimming the incident light, in a ring shape. Direct light incident on the phase plate 32 is transmitted through the phase ring. As a result, the phase of the direct light is shifted by ¼ wavelength, and the brightness is weakened. On the other hand, most of the diffracted light diffracted by the observation target S passes through a transparent plate portion of the phase plate 32. Accordingly, the phase and the brightness are not changed.

The objective lens 31 is moved in the Z direction (optical axis direction) under the control of a control unit 51 to be described later. In the case of capturing the phase difference image of the observation target S, autofocus control is performed by moving the objective lens 31 in the Z direction under the control of the control unit 51, so that the contrast of the image imaged by the imaging element 40 is adjusted.

In the present embodiment, pattern light is emitted to the culture container 60 by the focusing light emission unit 70, reflected light thereof is detected by the reflected light detection unit 75, and autofocus control is performed based on the detection signal. The autofocus control based on the detection signal of the reflected light of the pattern light will be described in detail later.

Direct light and diffracted light having passed through the phase plate 32 are incident on the imaging lens 33, and an image of these light beams is formed on the imaging element 40.

The imaging optical system 30 may be configured so that its optical magnification can be changed. As a method of changing the optical magnification, for example, a plurality of objective lenses 31 having different magnifications may be provided in the imaging optical system 30, and the plurality of objective lenses 31 may be automatically switched. In this case, the phase plate 32 is also changed according to the change of the objective lens 31. The magnification may be changed by the user manually exchanging the objective lens 31.

The imaging element 40 images the phase difference image of the observation target S imaged by the imaging lens 33. As the imaging element 40, a charge-coupled device (CCD) image sensor, a complementary metal-oxide semiconductor (CMOS) image sensor, or the like can be used.

The focusing light emission unit 70 is used for autofocus control as described above, and emits pattern light having a preset pattern, as light for autofocusing, to the culture container 60. Specifically, the focusing light emission unit 70 of the present embodiment emits pattern light having a striped pattern, and includes: a near-infrared light source 71 that emits near-infrared light; a grid 72 configured to include a linear portion that transmits near-infrared light emitted from the near-infrared light source 71 and a linear portion that shields the near-infrared light emitted from the near-infrared light source 71; an emission lens 73; and a dichroic mirror 74 that reflects pattern light having a pattern of bright and dark stripes emitted from the grid 72 toward the culture container 60 and transmits illumination light for phase difference measurement.

Although near-infrared light is used as the pattern light in the present embodiment, the wavelength of the pattern light is not limited thereto, and other wavelengths may be used as long as the wavelength is different from the illumination light for phase difference measurement.

The reflected light detection unit 75 detects reflected light due to emission of the pattern light to the culture container 60. Specifically, the reflected light detection unit 75 of the present embodiment includes a half mirror 76, an optical path difference prism 77, and a line sensor 78.

The half mirror 76 transmits the pattern light emitted from the grid 72, and reflects the reflected light due to emission of the pattern light to the culture container 60 in a direction of the optical path difference prism 77.

The optical path difference prism 77 divides the reflected light of the incident pattern light into two optical paths, and forms an image at two different places of the line sensor 78. The line sensor 78 outputs first and second detection signals, which are obtained by imaging at the two places, to the control unit 51 of the imaging control device 50. In the present embodiment, the reflected light beams of the two optical paths divided by the optical path difference prism 77 are detected by one line sensor 78. However, two sensors that individually detect the reflected light of each optical path may be provided.

The imaging control device 50 controls the operation of the imaging apparatus main body 10. As shown in FIG. 2, the imaging control device 50 includes the control unit 51 (corresponding to an imaging control unit of the invention) and a liquid droplet adhesion determination unit 52. The imaging control device 50 is a computer including a central processing unit (CPU), a semiconductor memory, a hard disk, and the like, and an embodiment of the imaging control program of the invention is installed on the hard disk. Then, the imaging control program is executed by the CPU, so that the control unit 51 and the liquid droplet adhesion determination unit 52 shown in FIG. 2 function. The imaging control program may be stored in an external non-transitory computer readable recording medium. In this case, the imaging control device 50 reads and executes the imaging control program stored in the recording medium.

The control unit 51 performs the autofocus control by moving the objective lens 31 in the Z direction based on the first and second detection signals detected by the line sensor 78 of the reflected light detection unit 75. Specifically, the control unit 51 determines a focal position by moving the objective lens 31 to a position where the contrast (waveform pattern) of the first detection signal and the contrast (waveform pattern) of the second detection signal are approximate to each other. Although the first and second detection signals are detected using the line sensor 78 in the present embodiment, a CMOS image sensor or a CCD image sensor may be used without being limited thereto.

The control unit 51 controls the driving of the stage driving unit 62 to move the stage 61 in the X, Y, and Z directions. By moving the stage 61 in the X and Y directions, for example, the inside of one well is scanned with illumination light for phase difference measurement, and a phase difference image is imaged for each of a plurality of imaging regions (visual field) divided in one well.

The liquid droplet adhesion determination unit 52 determines whether or not liquid droplet adhere to the bottom surface on the outer side of the culture container 60 based on the phase difference image of the observation target S imaged by the imaging apparatus main body 10.

Figure 3:
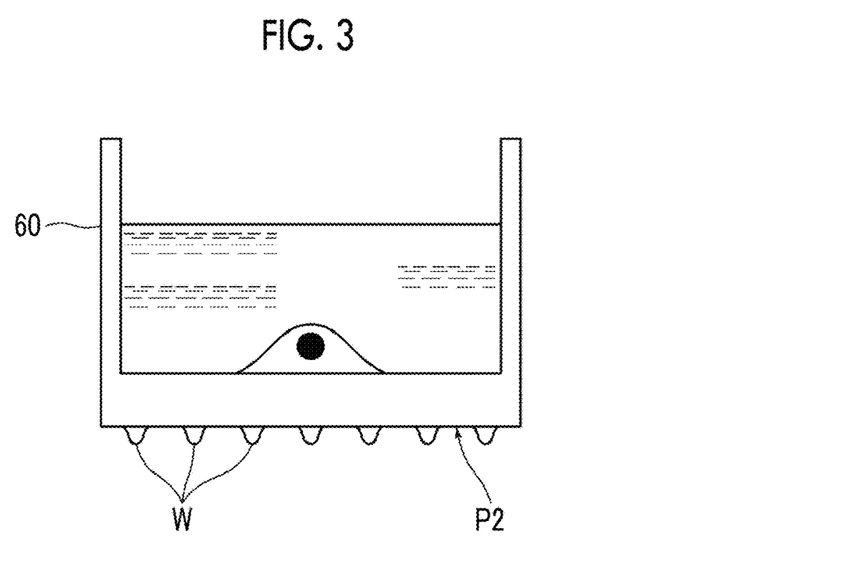
FIG. 3 is a schematic diagram how liquid droplets adhere to a bottom surface on the outer side of a culture container.

FIG. 3 is a schematic diagram showing how a liquid droplet W adheres to a bottom surface P2 on the outer side of the culture container 60. The liquid droplet W adheres to the bottom surface P2 due to dew condensation, which occurs due to differences in temperature and humidity between the incubator 15 and the outside air in a case where the culture container 60 is taken out from the incubator 15. The size of the liquid droplet W is a size that cannot be checked with the naked eye. However, on the phase difference image, the size of the droplet W can be checked since the contrast of light and dark is emphasized.

In a case where the liquid droplet W adheres to the bottom surface P2 of the culture container 60, the image of pattern light in the autofocus control is blurred due to the influence of the liquid droplet W. Therefore, it is not possible to perform appropriate autofocus control. In addition, even if the autofocus control is performed, there is a focus on the liquid droplet W instead of the observation target S. As a result, the phase difference image of a cell group that is the observation target S becomes a blurred image.

Therefore, in the microscope system of the present embodiment, the liquid droplet adhesion determination unit 52 determines whether or not liquid droplets adhere to the bottom surface P2 of the culture container 60. In a case where it is determined that the liquid droplet W adheres to the bottom surface P2, a phase difference image of the observation target S is imaged again after performing processing for removing the liquid droplet W.

The liquid droplet adhesion determination unit 52 of the present embodiment determines whether or not liquid droplets adhere to the bottom surface P2 on the outer side of the culture container 60 in two steps. Specifically, the liquid droplet adhesion determination unit 52 acquires spatial frequency components and a bright and dark pattern, which are included in the phase difference image, as pattern information of liquid droplets, and performs first determination for determining adhesion of liquid droplets based on the spatial frequency components and second determination for determining adhesion of liquid droplets based on the bright and dark pattern.

In the first determination, spatial frequency components included in the phase difference image are calculated. In a case where the amount of high-frequency components is small, that is, in a case where the phase difference image is blurred due to the adhesion of liquid droplets, it is determined that liquid droplets adhere to the bottom surface P2. On the other hand, in a case where the amount of high-frequency components is large, each cell in the culture container 60 is in focus, or liquid droplets adhering to the bottom surface of the culture container 60 are in focus. Therefore, the second determination is performed to determine which of each cell and each liquid droplet is in focus. The analysis of spatial frequency components may be performed by calculating the spectrum of the spatial frequency components included in the phase difference image, or may be performed by performing a Fourier transform or the like on the phase image, for example.

In the second determination, specifically, contour extraction processing for extracting the contour of each cell and the contour of the nucleus included in each cell from the phase difference image is performed. As the contour extraction processing, known processing, such as edge detection processing, can be used.

Figure 4:
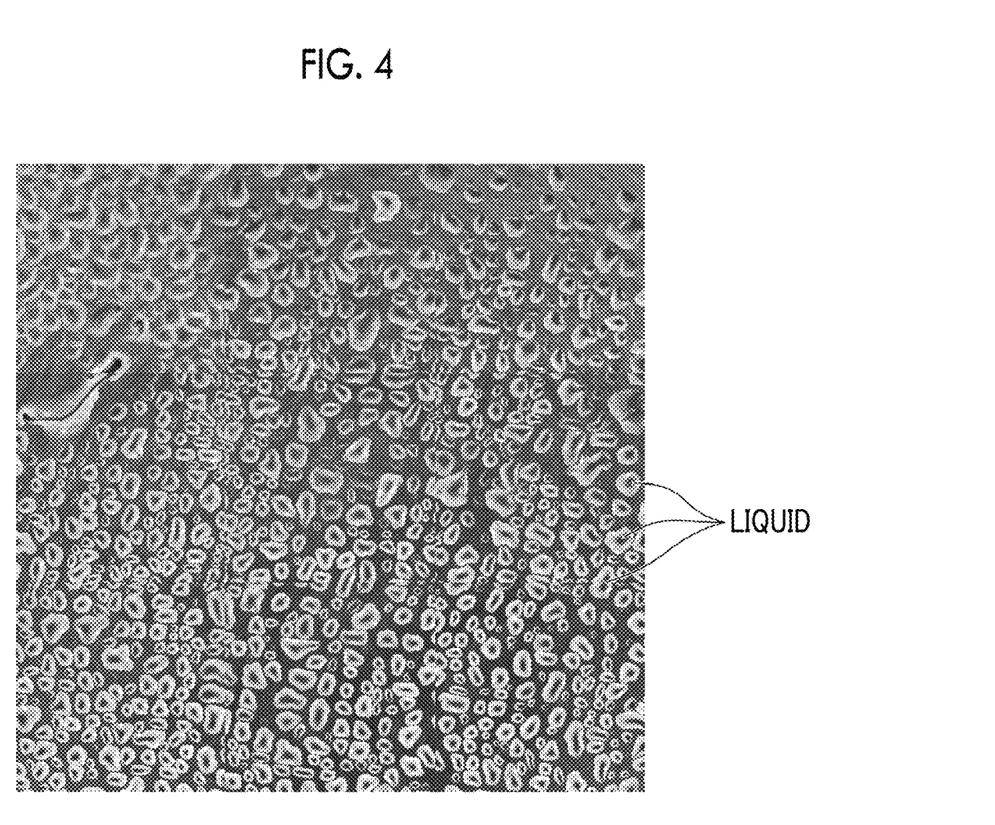
FIG. 4 is a diagram showing an example of a phase difference image of liquid droplets adhering to the bottom surface of the culture container.

As shown in FIG. 4, the phase difference image of liquid droplets adhering to the bottom surface of the culture container 60 has a bright and dark pattern in which the central portion is dark and the peripheral portion is bright. Therefore, the contour of the peripheral portion of the liquid droplet and the contour of the central dark portion can also be extracted by the contour extraction processing.

Also in the phase difference image of cells, a portion of nucleus is dark, and a portion of cytoplasm is bright. Accordingly, a bright and dark pattern is formed in the same manner as for the liquid droplet. However, in the bright and dark pattern of the liquid droplet, the contour of the surrounding bright portion and the contour of the central dark portion are similar to each other. In the case of cells, however, the nucleus of each cell is close to a circle, but the contour of the cytoplasm is not necessarily circular but has various forms. Therefore, in the second determination, it is determined whether each cell is in focus or each liquid droplet is in focus using the difference.

Specifically, it is determined whether or not the outer contour and the inner contour of the bright and dark pattern of each cell or each liquid droplet formed from the contour extracted from the phase difference image are similar to each other, and it is further determined whether or not the area ratio between a dark portion and a bright portion in the bright and dark pattern is within a preset threshold range. For the determination regarding whether or not the outer contour and the inner contour of the bright and dark pattern are similar to each other, for example, the degree of similarity between the outer contour and the inner contour of each bright and dark pattern may be calculated, and it may be determined whether or not the degree of similarity is equal to or greater than a preset threshold value. For the area ratio between the dark portion and the bright portion in the bright and dark pattern, for example, a ratio between the total area of dark portions and the total area of bright portions in the bright and dark pattern of each cell or each liquid droplet may be calculated.

Then, in the second determination, in a case where the outer contour and the inner contour of the bright and dark pattern are similar to each other and the area ratio between the dark portion and the bright portion in the bright and dark pattern is within the preset threshold range, a possibility that the bright and dark pattern is a pattern of liquid droplets is high. Accordingly, it is determined that the liquid droplets are in focus. On the other hand, in a case where one of the above conditions is not satisfied, it is determined that each cell is in focus.

Then, in the second determination, the liquid droplet adhesion determination unit 52 determines that the liquid droplets adhere to the bottom surface on the outer side of the culture container 60 by determining that the liquid droplets are in focus.

The determination result of the liquid droplet adhesion determination unit 52 is output to the control unit 51. In a case where it is determined that liquid droplets adhere to the bottom surface on the outer side of the culture container 60, the control unit 51 performs preset liquid droplet removal processing and then images a phase difference image of the observation target S again.

The liquid droplet removal processing in the present embodiment is processing for returning the culture container 60 from the stage 61 of the imaging apparatus main body 10 into the incubator 15 and leaving the culture container 60 in the incubator 15 for a preset time. By leaving the culture container 60 in the incubator 15 in this manner, it is possible to remove liquid droplets adhering to the bottom surface of the culture container 60.

After the above-described liquid droplet removal processing is performed, the control unit 51 places the culture container 60 again on the stage 61 of the imaging apparatus main body 10 from the incubator 15 and images the observation target S again. During the re-imaging, it is preferable that the transport speed of the culture container 60 from the incubator 15 onto the stage 61 of the imaging apparatus main body 10 is higher than the transport speed at the time of the first imaging. This makes it possible to prevent liquid droplets from re-adhering to the culture container 60.

Referring back to FIG. 1, the input device 90 and the display device 80 are connected to the imaging control device 50. The input device 90 includes an input device, such as a keyboard or a mouse, and receives a setting input from the user. In particular, the input device 90 in the present embodiment receives a setting inputs, such as information of the magnification of the objective lens 31 described above.

The display device 80 is a display device, such as a liquid crystal display, and displays a phase difference image or the like imaged by the imaging element 40. The display device 80 may also be used as the input device 90 by using a touch panel as the display device 80.

Figure 5:
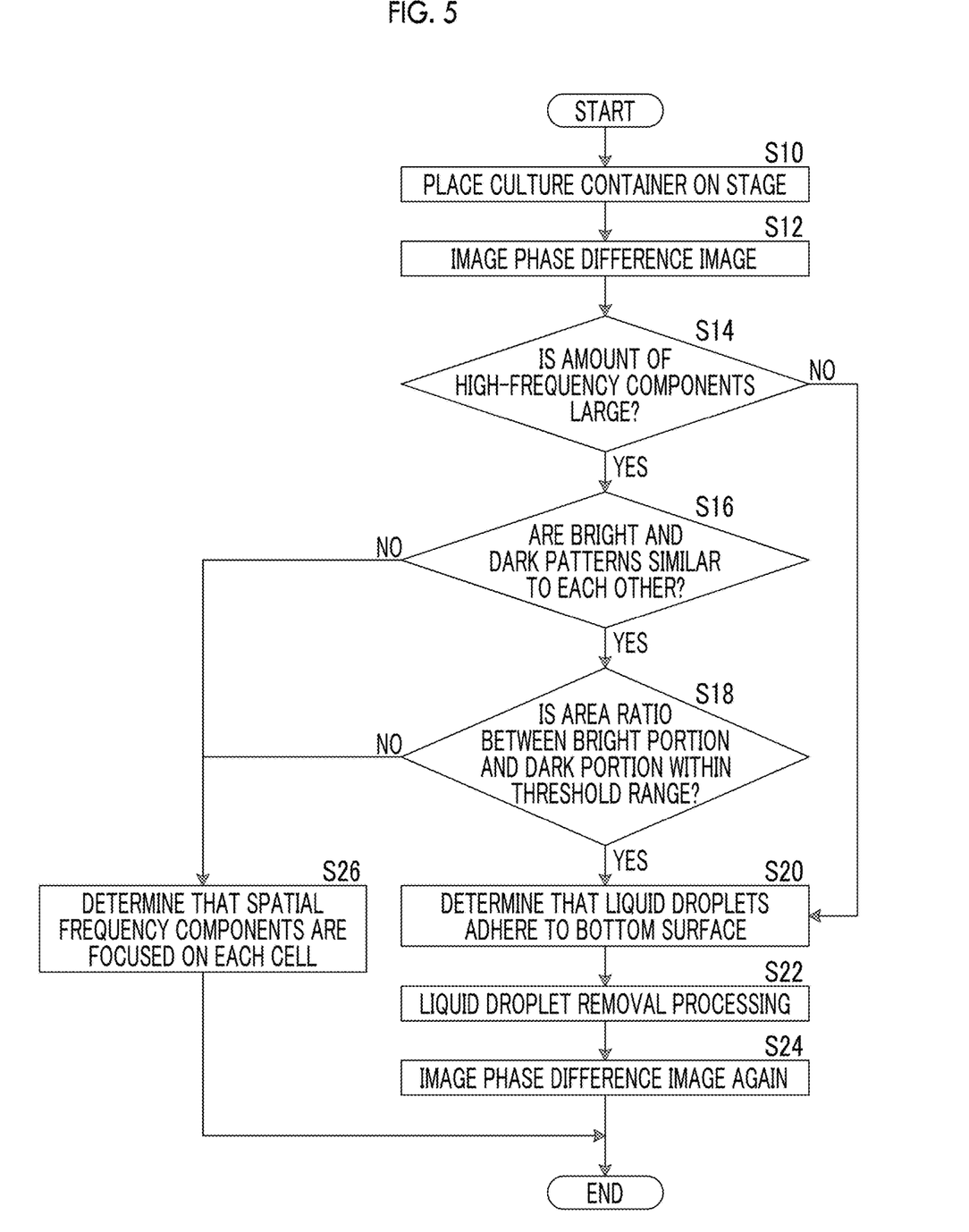
FIG. 5 is a flowchart illustrating the operation of the microscope system using an embodiment of the imaging apparatus of the invention.

Next, the operation of the microscope system of the present embodiment will be described with reference to the flowchart shown in FIG. 5.

First, the culture container 60 in which the observation target S is contained is taken out from the incubator 15 and is placed on the stage 61 (S10).

Then, autofocus control is performed by emitting the pattern light, which is emitted from the focusing light emission unit 70, to the culture container 60, so that a phase difference image of the observation target S is imaged (S12).

The phase difference image imaged by the imaging element 40 is input to the liquid droplet adhesion determination unit 52. Then, the liquid droplet adhesion determination unit 52 first calculates spatial frequency components included in the phase difference image, and performs the first determination for determining whether or not a large amount of high-frequency components are included (S14). In a case where the amount of high-frequency components is small and the phase difference image is a blurred image (S14, NO), the liquid droplet adhesion determination unit 52 determines that liquid droplets adhere to the bottom surface of the culture container 60 (S20), and proceeds to the liquid droplet removal processing of S22.

On the other hand, in a case where a large amount of high-frequency components are included in the phase difference image (YES in S14), the liquid droplet adhesion determination unit 52 performs the second determination. In the second determination, first, it is determined whether or not the outer contour and the inner contour of the bright and dark pattern included in the phase difference image are similar to each other (S16). Then, in a case where it is determined that the outer contour and the inner contour of the bright and dark pattern included in the phase difference image are similar to each other (YES in S16), it is determined whether or not the area ratio between a dark portion and a bright portion in the bright and dark pattern is within a preset threshold range (S18). Then, in a case where it is determined the area ratio between the dark portion and the bright portion in the bright and dark pattern is within a preset threshold range (YES in S18), the liquid droplet adhesion determination unit 52 determines that liquid droplets are in focus, and determines that the liquid droplets adhere to the bottom surface on the outer side of the culture container 60 (S20).

Then, in a case where the liquid droplet adhesion determination unit 52 determines that liquid droplets adhere to the bottom surface on the outer side of the culture container 60 (S20), liquid droplet removal processing is performed (S22). Specifically, as described above, the culture container 60 is returned from the stage 61 of the imaging apparatus main body 10 into the incubator 15, and is left for a preset time.

After the liquid droplet removal processing is performed, the culture container 60 is taken out from the incubator 15 and is placed again on the stage 61 of the imaging apparatus main body 10, so that the phase difference image of the observation target S is imaged again (S24). The re-imaged phase difference image of the observation target S is displayed on the display device 80 by the control unit 51.

On the other hand, in a case where it is determined that the outer contour and the inner contour of the bright and dark pattern are not similar to each other in S16 (NO in S16) or in a case where it is determined that the area ratio between the dark portion and the bright portion in the bright and dark pattern is not within the preset threshold range in S18 (NO in S18), it is determined that each cell, which is the observation target S, is in focus (S26). That is, it is determined that an appropriate phase difference image has been imaged without liquid droplets adhering to the bottom surface of the culture container 60. In this case, the control unit 51 displays the phase difference image imaged for the first time on the display device 80 without performing the liquid droplet removal processing and the re-capturing of the phase difference image described above.

According to the microscope system of the embodiment described above, the observation target S contained in the culture container 60 is imaged, the pattern information of liquid droplets adhering to the bottom surface on the outer side of the culture container 60 is acquired based on the phase difference image of the imaged observation target S, it is determined whether or not liquid droplets adhere to the bottom surface on the outer side of the culture container 60 based on the pattern information, and the observation target S is imaged again after the preset liquid droplet removal processing is performed in a case where it is determined that liquid droplets adhere to the bottom surface on the outer side of the culture container 60. Therefore, it is possible to suppress blurring due to liquid droplets that adhere to the bottom surface on the outer side of the culture container 60 and have sizes that cannot be checked with the naked eye.

In the microscope system of the embodiment described above, a bright and dark pattern is extracted by performing contour extraction processing, such as edge detection, and it is determined whether or not liquid droplets adhere to the bottom surface based on the bright and dark pattern. However, the invention is not limited thereto. For example, a pattern of liquid droplets may be acquired in advance, pattern information indicating whether or not liquid droplets are included in the phase difference image may be acquired by performing pattern recognition using the pattern of liquid droplets, and it is determined whether or not liquid droplets adhere to the bottom surface on the outer side of the culture container 60 based on the pattern information. In the case of performing pattern recognition in this manner, a discriminator in which a pattern of liquid droplets is machine-learned may be generated, and the pattern of liquid droplets may be recognized using the discriminator. As a machine learning method, AdaBoost and support vector machine can be used.

In the microscope system of the embodiment described above, processing for returning the culture container 60 into the incubator 15 and leaving the culture container 60 therein is performed as the liquid droplet removal processing. In this case, the humidity in the incubator 15 may be lowered or the temperature in the incubator 15 may be increased so that liquid droplets evaporate quickly.

Figure 6:
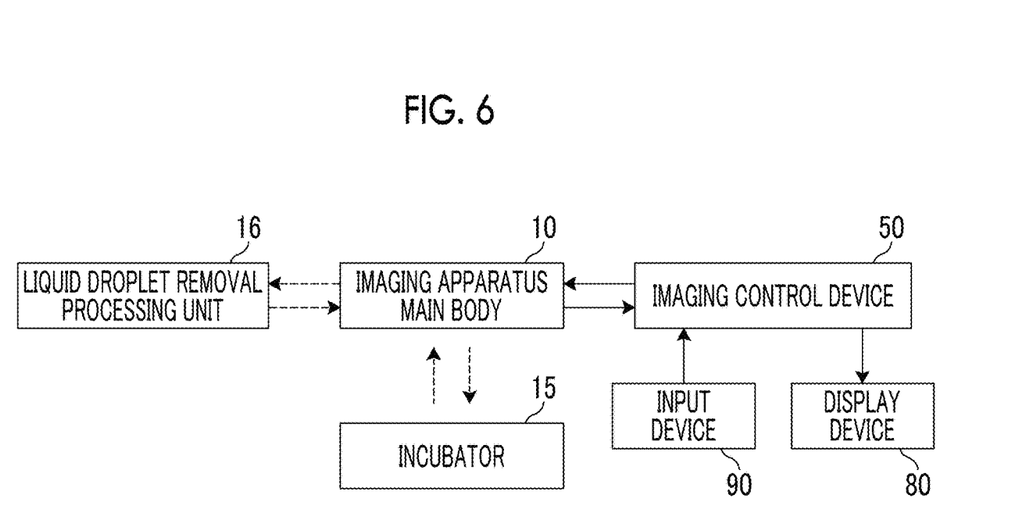
FIG. 6 is a block diagram showing the schematic configuration of a microscope system using another embodiment of the imaging apparatus of the invention.

Without being returned to the incubator 15, the culture container 60 may be left on the stage 61 for a preset time and then re-imaging may be performed. The liquid droplet removal processing is not limited thereto, and a liquid droplet removal processing unit 16 that performs liquid droplet removal processing may be provided as shown in FIG. 6.

As a configuration of the liquid droplet removal processing unit 16, for example, a wiping unit for wiping out liquid droplets on the bottom surface on the outer side of the culture container 60 may be provided. As the wiping unit, for example, a cloth for wiping out liquid droplets and a moving mechanism for moving the cloth within the XY plane while pressing the cloth against the bottom surface on the outer side of the culture container 60 may be provided.

The liquid droplet removal processing unit 16 may have a heating unit for increasing the temperature of the bottom surface of the culture container 60. As the heating unit, for example, a known configuration, such as a heating wire, can be used. By increasing the temperature of the bottom surface of the culture container 60 using the heating unit, liquid droplets can be evaporated.

The liquid droplet removal processing unit 16 may have an air supply unit for supplying air toward the bottom surface of the culture container 60. As the air supply unit, for example, a known configuration, such as a fan, can be used. By supplying air to the bottom surface of the culture container 60 using the air supply unit, liquid droplets can be evaporated.

The liquid droplet removal processing unit 16 may be provided in the incubator 15 or the imaging apparatus main body 10.

In a case where the liquid droplet adhesion determination unit 52 determines that liquid droplets adhere to the bottom surface, the control unit 51 may warn the user, for example, by displaying a message on the display device 80. Then, the liquid droplet removal processing may be manually performed by the user.

A threshold value used in a case where the liquid droplet adhesion determination unit 52 determines whether or not liquid droplets adhere to the bottom surface may be configured to be changeable. Examples of the threshold value include a threshold value in the case of determining whether or not a large amount of high-frequency components are included in spatial frequency components included in the phase difference image and a threshold range in the case of determining whether or not the area ratio between the dark portion and the bright portion in the bright and dark pattern is within the preset threshold range. However, the threshold value is not limited thereto, and other threshold values may be configured to be changeable as long as these are threshold values used for determination. For changing the threshold value, for example, a threshold value change screen may be displayed on the display device 80, so that a changed threshold value is received through the input device 90.

Figure 7:
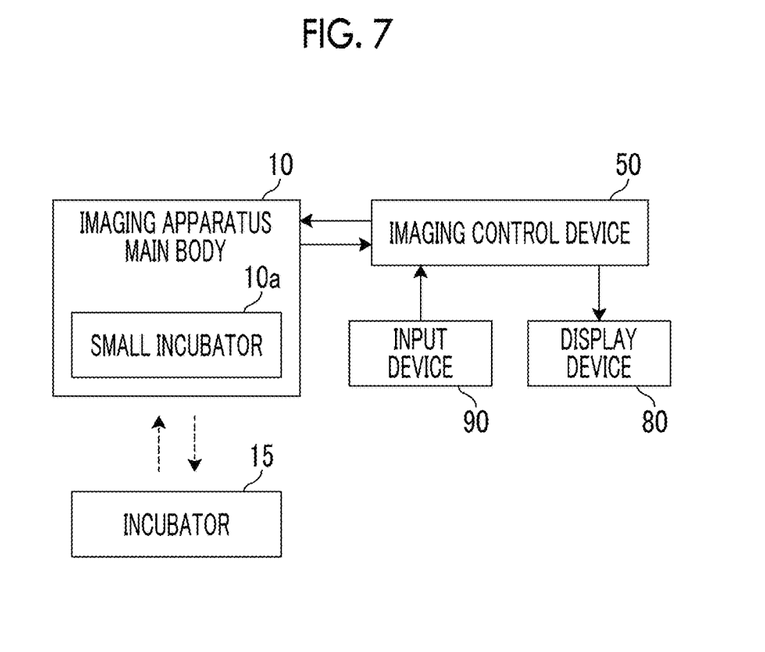
FIG. 7 is a block diagram showing the schematic configuration of a microscope system using another embodiment of the imaging apparatus of the invention.

As shown in FIG. 7, a small incubator 10a may be provided in the imaging apparatus main body 10. Then, in a case where the liquid droplet adhesion determination unit 52 determines that liquid droplets adhere to the bottom surface, the liquid droplet removal processing may be performed by leaving the culture container 60 in the small incubator 10a for a preset time. Alternatively, the liquid droplet removal processing may be performed by lowering the humidity in the small incubator 10a or increasing the temperature in the small incubator 10a. In addition, it is preferable that the transport time of the culture container 60 from the incubator 15 to the small incubator 10a is as short as possible.

Although the autofocus control is performed in the microscope system of the embodiment described above, the autofocus control may not be performed.

In the above embodiment, the invention is applied to the phase contrast microscope. However, the invention is not limited to the phase contrast microscope, but may be applied to other microscopes, such as a differential interference microscope and a bright field microscope.

EXPLANATION OF REFERENCES

10: imaging apparatus main body
11: white light source
12: slit plate
13: condenser lens
15: incubator
16: liquid droplet removal processing unit
20: illumination light emission unit
30: imaging optical system 31: objective lens
32: phase plate
33: imaging lens
40: imaging element
50: imaging control device
51: control unit
52: liquid droplet adhesion determination unit
60: culture container
61: stage
62: stage driving unit
70: focusing light emission unit
71: near-infrared light source
72: grid
73: emission lens
74: dichroic mirror
75: reflected light detection unit
76: half mirror
77: optical path difference prism
78: line sensor
80: display device
90: input device
C: culture solution
P1: observation target placement surface
P2: bottom surface
S: observation target
W: liquid droplet

What is claimed is:

1. An imaging apparatus, comprising:
an imaging unit that images an observation target contained in a container; and
a liquid droplet adhesion determination unit that acquires pattern information of liquid droplets adhering to a bottom surface on an outer side of the container based on an image of the observation target imaged by the imaging unit and determines whether or not the liquid droplets adhere to the bottom surface based on the pattern information,
wherein, in a case where the liquid droplet adhesion determination unit determines that the liquid droplets adhere to the bottom surface on the outer side of the container, the imaging unit images the observation target again after performing a liquid droplet removal processing.

2. The imaging apparatus according to claim 1,
wherein the imaging unit images the observation target by performing autofocus control.

3. The imaging apparatus according to claim 1,
wherein the liquid droplet adhesion determination unit acquires spatial frequency components included in the image as the pattern information, and determines whether or not the liquid droplets adhere to the bottom surface on the outer side of the container based on the spatial frequency components.

4. The imaging apparatus according to claim 2,
wherein the liquid droplet adhesion determination unit acquires spatial frequency components included in the image as the pattern information, and determines whether or not the liquid droplets adhere to the bottom surface on the outer side of the container based on the spatial frequency components.

5. The imaging apparatus according to claim 1,
wherein the liquid droplet adhesion determination unit acquires a bright and dark pattern included in the image as the pattern information, and determines whether or not the liquid droplets adhere to the bottom surface on the outer side of the container based on the bright and dark pattern.

6. The imaging apparatus according to claim 2,
wherein the liquid droplet adhesion determination unit acquires a bright and dark pattern included in the image as the pattern information, and determines whether or not the liquid droplets adhere to the bottom surface on the outer side of the container based on the bright and dark pattern.

7. The imaging apparatus according to claim 3,
wherein the liquid droplet adhesion determination unit acquires a bright and dark pattern included in the image as the pattern information, and determines whether or not the liquid droplets adhere to the bottom surface on the outer side of the container based on the bright and dark pattern.

8. The imaging apparatus according to claim 4,
wherein the liquid droplet adhesion determination unit acquires a bright and dark pattern included in the image as the pattern information, and determines whether or not the liquid droplets adhere to the bottom surface on the outer side of the container based on the bright and dark pattern.

9. The imaging apparatus according to claim 1,
wherein the liquid droplet adhesion determination unit acquires spatial frequency components and a bright and dark pattern, which are included in the image, as the pattern information, and determines whether or not the liquid droplets adhere to the bottom surface on the outer side of the container by performing first determination based on the spatial frequency components and then performing second determination based on the bright and dark pattern.

10. The imaging apparatus according to claim 2,
wherein the liquid droplet adhesion determination unit acquires spatial frequency components and a bright and dark pattern, which are included in the image, as the pattern information, and determines whether or not the liquid droplets adhere to the bottom surface on the outer side of the container by performing first determination based on the spatial frequency components and then performing second determination based on the bright and dark pattern.

11. The imaging apparatus according to claim 1,
wherein the liquid droplet adhesion determination unit acquires the pattern information by recognizing a pattern of the liquid droplets included in the image, and determines whether or not the liquid droplets adhere to the bottom surface on the outer side of the container based on the pattern information.

12. The imaging apparatus according to claim 2,
wherein the liquid droplet adhesion determination unit acquires the pattern information by recognizing a pattern of the liquid droplets included in the image, and determines whether or not the liquid droplets adhere to the bottom surface on the outer side of the container based on the pattern information.

13. The imaging apparatus according to claim 11,
wherein the liquid droplet adhesion determination unit has a machine-learned discriminator for discriminating the liquid droplets, and recognizes the pattern of the liquid droplets using the discriminator.

14. The imaging apparatus according to claim 1,
wherein the liquid droplet removal processing is processing for leaving the container in an incubator, in which the container is contained, for a preset time.

15. The imaging apparatus according to claim 1, further comprising:

a liquid droplet removal processing unit that performs the liquid droplet removal processing.

16. The imaging apparatus according to claim 15, wherein the liquid droplet removal processing unit has a wiping unit for wiping out the liquid droplets on the bottom surface on the outer side of the container.

17. The imaging apparatus according to claim 15, wherein the liquid droplet removal processing unit has a heating unit for increasing a temperature of the bottom surface of the container.

18. The imaging apparatus according to claim 15, wherein the liquid droplet removal processing unit has an air supply unit for supplying air toward the bottom surface of the container.

19. An imaging method, comprising:
imaging an observation target contained in a container;
acquiring pattern information of liquid droplets adhering to a bottom surface on an outer side of the container based on an image of the imaged observation target and determining whether or not the liquid droplets adhere to the bottom surface based on the pattern information; and
imaging the observation target again after performing a liquid droplet removal processing in a case where it is determined that the liquid droplets adhere to the bottom surface on the outer side of the container.

20. A non-transitory computer readable recording medium storing an imaging control program causing a computer to function as:
an imaging control unit that controls an imaging unit to image an observation target contained in a container; and
a liquid droplet adhesion determination unit that acquires pattern information of liquid droplets adhering to a bottom surface on an outer side of the container based on an image of the observation target imaged by the imaging unit and determines whether or not the liquid droplets adhere to the bottom surface based on the pattern information,
wherein, in a case where the liquid droplet adhesion determination unit determines that the liquid droplets adhere to the bottom surface on the outer side of the container, the imaging control unit controls the imaging unit to image the observation target again after performing a liquid droplet removal processing.

* * * * *